(12) United States Patent
Starksen et al.

(10) Patent No.: US 7,534,204 B2
(45) Date of Patent: May 19, 2009

(54) CARDIAC VISUALIZATION DEVICES AND METHODS

(75) Inventors: Niel F. Starksen, Los Altos Hills, CA (US); Nick Pliam, Kent, CT (US); Rodolfo A. Morales, Los Gatos, CA (US); John To, Newark, CA (US)

(73) Assignee: Guided Delivery Systems, Inc., Santa Clara, CA (US)

( * ) Notice: Subject to any disclaimer, the term of this patent is extended or adjusted under 35 U.S.C. 154(b) by 463 days.

(21) Appl. No.: 10/927,784

(22) Filed: Aug. 27, 2004

(65) Prior Publication Data
US 2005/0119523 A1 Jun. 2, 2005

Related U.S. Application Data

(60) Provisional application No. 60/500,773, filed on Sep. 3, 2003.

(51) Int. Cl.
*A61B 1/00* (2006.01)
(52) U.S. Cl. .................. 600/116; 600/129; 600/182
(58) Field of Classification Search ............ 600/104, 600/115, 116, 127, 175, 129, 130, 182, 156; 604/102.01, 102.02, 915, 917; 606/7, 15
See application file for complete search history.

(56) References Cited

U.S. PATENT DOCUMENTS

| | | | |
|---|---|---|---|
| 3,773,034 A | 11/1973 | Burns et al. | |
| 3,961,419 A | 6/1976 | Schwartz | |
| 3,976,079 A | 8/1976 | Samuels et al. | |
| 4,014,492 A | 3/1977 | Rothfuss | |
| 4,034,473 A | 7/1977 | May | |
| 4,042,979 A | 8/1977 | Angell | |
| 4,043,504 A | 8/1977 | Hueil et al. | |

(Continued)

FOREIGN PATENT DOCUMENTS

EP 0 669 101 A1 8/1995

(Continued)

OTHER PUBLICATIONS

International Search Report mailed Dec. 19, 2006, for PCT Application No. PCT/US2006/031190, filed Aug. 10, 2006, four pages.

(Continued)

*Primary Examiner*—John P Leubecker
*Assistant Examiner*—Victoria W Chen
(74) *Attorney, Agent, or Firm*—Morrison & Foerster LLP (57) ABSTRACT

Devices and methods for facilitating transvascular, minimally invasive and other "less invasive" surgical procedures generally include a sheath with an expandable balloon at the distal end, an inflation lumen for expanding the balloon, and a device passage lumen for allowing passage of one or more surgical instruments. The sheath is configured to house at least one visualization device such that an optical element of the device is positioned to view the surgical site. In some embodiments, instruments may be passed through the sheath, with the distal balloon partially or fully circumscribing or encircling the instruments. Any suitable instrument(s) may be passed through sheaths of the invention, such as a surgical clip applier for repairing a heart valve, an ablation member for treating atrial fibrillation, one or more pacemaker leads, a coronary sinus access device or the like.

12 Claims, 4 Drawing Sheets

U.S. PATENT DOCUMENTS

| | | | |
|---|---|---|---|
| 4,053,979 A | 10/1977 | Tuthill et al. | |
| 4,055,861 A | 11/1977 | Carpentier et al. | |
| 4,069,825 A | 1/1978 | Akiyama | |
| 4,384,406 A | 5/1983 | Tischlinger | |
| 4,445,892 A * | 5/1984 | Hussein et al. | 604/101.05 |
| 4,494,542 A | 1/1985 | Lee | |
| 4,619,247 A * | 10/1986 | Inoue et al. | 600/116 |
| 4,700,250 A | 10/1987 | Kuriyama | |
| 4,726,371 A | 2/1988 | Gibbens | |
| 4,758,221 A | 7/1988 | Jureidini | |
| 4,784,133 A * | 11/1988 | Mackin | 606/7 |
| 4,845,851 A | 7/1989 | Warthen | |
| 4,848,341 A | 7/1989 | Ahmad | |
| 4,850,354 A | 7/1989 | McGurk-Burleson et al. | |
| 4,961,738 A * | 10/1990 | Mackin | 606/15 |
| 4,969,893 A | 11/1990 | Swor | |
| 4,976,710 A * | 12/1990 | Mackin | 606/15 |
| 5,053,047 A | 10/1991 | Yoon | |
| 5,084,058 A | 1/1992 | Li | |
| 5,103,804 A * | 4/1992 | Abele et al. | 600/116 |
| 5,133,723 A | 7/1992 | Li et al. | |
| 5,203,337 A * | 4/1993 | Feldman | 600/463 |
| 5,221,255 A | 6/1993 | Mahurkar et al. | |
| 5,242,456 A | 9/1993 | Nash et al. | |
| 5,257,975 A | 11/1993 | Foshee | |
| 5,312,341 A * | 5/1994 | Turi | 604/103.05 |
| 5,346,500 A | 9/1994 | Suchart | |
| 5,358,479 A | 10/1994 | Wilson | |
| 5,364,407 A | 11/1994 | Poll | |
| 5,366,479 A | 11/1994 | McGarry et al. | |
| 5,368,591 A | 11/1994 | Lennox et al. | |
| 5,383,905 A | 1/1995 | Golds et al. | |
| 5,409,483 A * | 4/1995 | Campbell et al. | 606/15 |
| 5,417,700 A | 5/1995 | Egan | |
| 5,423,837 A | 6/1995 | Mericle et al. | |
| 5,437,680 A | 8/1995 | Yoon | |
| 5,439,470 A | 8/1995 | Li | |
| 5,450,860 A | 9/1995 | O'Connor | |
| 5,452,513 A | 9/1995 | Zinnbauer et al. | |
| 5,474,572 A | 12/1995 | Hayhurst | |
| 5,520,702 A | 5/1996 | Sauer et al. | |
| 5,522,873 A | 6/1996 | Jackman et al. | |
| 5,524,630 A | 6/1996 | Crowley | |
| 5,545,134 A * | 8/1996 | Hilaire et al. | 604/103.04 |
| 5,545,168 A | 8/1996 | Burke | |
| 5,565,122 A | 10/1996 | Zinnbauer et al. | |
| 5,569,241 A | 10/1996 | Edwards | |
| 5,571,215 A | 11/1996 | Sterman et al. | |
| 5,591,194 A * | 1/1997 | Berthiaume | 606/192 |
| 5,626,614 A | 5/1997 | Hart | |
| 5,630,824 A | 5/1997 | Hart | |
| 5,643,289 A | 7/1997 | Sauer et al. | |
| 5,669,917 A | 9/1997 | Sauer et al. | |
| 5,674,279 A | 10/1997 | Wright et al. | |
| 5,690,655 A | 11/1997 | Hart et al. | |
| 5,709,695 A | 1/1998 | Northrup, III | |
| 5,716,370 A | 2/1998 | Williamson, IV et al. | |
| 5,722,403 A * | 3/1998 | McGee et al. | 600/373 |
| 5,725,542 A | 3/1998 | Yoon | |
| 5,741,260 A | 4/1998 | Songer et al. | |
| 5,741,301 A | 4/1998 | Pagedas | |
| 5,752,518 A | 5/1998 | McGee et al. | |
| 5,752,964 A | 5/1998 | Mericle | |
| 5,752,966 A | 5/1998 | Chang | |
| 5,755,730 A | 5/1998 | Swain et al. | |
| 5,766,240 A | 6/1998 | Johnson | |
| 5,769,812 A | 6/1998 | Stevens et al. | |
| 5,779,673 A * | 7/1998 | Roth et al. | 604/101.03 |
| 5,810,848 A | 9/1998 | Hayhurst | |
| 5,810,853 A | 9/1998 | Yoon | |
| 5,827,171 A * | 10/1998 | Dobak et al. | 600/16 |
| 5,843,169 A | 12/1998 | Taheri | |
| 5,848,969 A | 12/1998 | Panescu et al. | |
| 5,849,035 A * | 12/1998 | Pathak et al. | 128/898 |
| 5,860,992 A | 1/1999 | Daniel et al. | |
| 5,860,993 A | 1/1999 | Thompson et al. | |
| 5,868,733 A | 2/1999 | Ockuly et al. | |
| 5,873,877 A | 2/1999 | McGaffigan et al. | |
| 5,879,371 A | 3/1999 | Gardiner et al. | |
| 5,885,238 A | 3/1999 | Stevens et al. | |
| 5,888,240 A | 3/1999 | Carpentier et al. | |
| 5,902,321 A | 5/1999 | Caspari et al. | |
| 5,904,651 A | 5/1999 | Swanson et al. | |
| 5,919,208 A | 7/1999 | Valenti | |
| 5,935,149 A | 8/1999 | Ek | |
| 5,961,539 A | 10/1999 | Northrup, III et al. | |
| 5,972,004 A | 10/1999 | Williamson, IV et al. | |
| 5,989,284 A | 11/1999 | Laufer | |
| 5,991,650 A | 11/1999 | Swanson et al. | |
| 6,010,531 A | 1/2000 | Donlon et al. | |
| 6,015,428 A | 1/2000 | Pagedas | |
| 6,056,744 A | 5/2000 | Edwards | |
| 6,066,160 A | 5/2000 | Colvin et al. | |
| 6,074,401 A | 6/2000 | Gardiner et al. | |
| 6,077,989 A | 6/2000 | Kandel et al. | |
| 6,097,985 A | 8/2000 | Kasevich et al. | |
| 6,099,553 A | 8/2000 | Hart et al. | |
| 6,149,658 A | 11/2000 | Gardiner et al. | |
| 6,165,183 A | 12/2000 | Kuehn et al. | |
| 6,193,714 B1 | 2/2001 | McGaffigan et al. | |
| 6,197,017 B1 | 3/2001 | Brock et al. | |
| 6,228,096 B1 | 5/2001 | Marchand | |
| 6,250,308 B1 | 6/2001 | Cox | |
| 6,254,620 B1 | 7/2001 | Koh et al. | |
| 6,258,118 B1 | 7/2001 | Baum et al. | |
| 6,260,552 B1 | 7/2001 | Mortier et al. | |
| 6,269,819 B1 | 8/2001 | Oz et al. | |
| 6,283,993 B1 | 9/2001 | Cosgrove et al. | |
| 6,306,149 B1 | 10/2001 | Meade | |
| 6,312,447 B1 | 11/2001 | Grimes | |
| 6,328,727 B1 | 12/2001 | Frazier et al. | |
| 6,332,893 B1 | 12/2001 | Mortier et al. | |
| 6,355,030 B1 | 3/2002 | Aldrich et al. | |
| 6,378,289 B1 | 4/2002 | Trudeau et al. | |
| 6,409,743 B1 | 6/2002 | Fenton, Jr. | |
| 6,423,088 B1 | 7/2002 | Fenton, Jr. | |
| 6,432,123 B2 | 8/2002 | Schwartz et al. | |
| 6,461,327 B1 * | 10/2002 | Addis et al. | 604/101.04 |
| 6,514,265 B2 | 2/2003 | Ho et al. | |
| 6,524,338 B1 | 2/2003 | Gundry | |
| 6,533,753 B1 * | 3/2003 | Haarstad et al. | 604/96.01 |
| 6,551,332 B1 | 4/2003 | Nguyen et al. | |
| 6,575,971 B2 | 6/2003 | Hauck et al. | |
| 6,602,288 B1 | 8/2003 | Cosgrove et al. | |
| 6,602,289 B1 | 8/2003 | Colvin et al. | |
| 6,607,541 B1 | 8/2003 | Gardiner et al. | |
| 6,613,059 B2 | 9/2003 | Schaller et al. | |
| 6,619,291 B2 | 9/2003 | Hlavka et al. | |
| 6,626,899 B2 | 9/2003 | Houser et al. | |
| 6,629,534 B1 | 10/2003 | St. Goar et al. | |
| 6,641,593 B1 | 11/2003 | Schaller et al. | |
| 6,648,903 B1 | 11/2003 | Pierson, III | |
| 6,651,671 B1 | 11/2003 | Donlon et al. | |
| 6,655,386 B1 | 12/2003 | Makower et al. | |
| 6,669,687 B1 | 12/2003 | Saadat | |
| 6,676,702 B2 | 1/2004 | Mathis | |
| 6,689,164 B1 | 2/2004 | Seguin | |
| 6,699,263 B2 | 3/2004 | Cope | |
| 6,702,826 B2 | 3/2004 | Liddicoat et al. | |
| 6,716,243 B1 | 4/2004 | Colvin et al. | |
| 6,718,985 B2 | 4/2004 | Hlavka et al. | |
| 6,733,509 B2 | 5/2004 | Nobles et al. | |
| 6,752,813 B2 | 6/2004 | Goldfarb et al. | |
| 6,790,231 B2 | 9/2004 | Liddicoat et al. | |

| | | |
|---|---|---|
| 6,923,818 B2 | 8/2005 | Muramatsu et al. |
| 6,932,792 B1 * | 8/2005 | St. Goar et al. .......... 604/96.01 |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,048,754 B2 | 5/2006 | Martin et al. |
| 7,101,395 B2 | 9/2006 | Tremulis et al. |
| 7,166,127 B2 | 1/2007 | Spence et al. |
| 7,186,262 B2 | 3/2007 | Saadat |
| 7,235,086 B2 | 6/2007 | Sauer et al. |
| 7,241,310 B2 | 7/2007 | Taylor et al. |
| 2001/0005787 A1 | 6/2001 | Oz et al. |
| 2001/0014800 A1 | 8/2001 | Frazier et al. |
| 2001/0023332 A1 * | 9/2001 | Hahnen ................... 604/98.01 |
| 2001/0031979 A1 | 10/2001 | Ricci |
| 2002/0013621 A1 | 1/2002 | Stobie et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 * | 7/2002 | Brock et al. ................. 606/139 |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 * | 11/2002 | Bertolero et al. ....... 604/102.01 |
| 2002/0173841 A1 | 11/2002 | Ortiz et al. |
| 2002/0193815 A1 | 12/2002 | Foerster et al. |
| 2003/0009196 A1 | 1/2003 | Peterson |
| 2003/0018358 A1 | 1/2003 | Saadat |
| 2003/0033006 A1 | 2/2003 | Phillips et al. |
| 2003/0060813 A1 | 3/2003 | Loeb et al. |
| 2003/0069593 A1 | 4/2003 | Tremulis et al. |
| 2003/0074012 A1 | 4/2003 | Nguyen et al. |
| 2003/0078465 A1 | 4/2003 | Pai et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 * | 8/2003 | Bertolero ................... 600/116 |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0199974 A1 | 10/2003 | Lee et al. |
| 2003/0220685 A1 | 11/2003 | Hlavka et al. |
| 2003/0225420 A1 | 12/2003 | Wardle |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0030382 A1 | 2/2004 | St. Goar et al. |
| 2004/0039442 A1 | 2/2004 | St. Goar et al. |
| 2004/0093044 A1 * | 5/2004 | Rychnovsky et al. ......... 607/88 |
| 2004/0097788 A1 * | 5/2004 | Mourlas et al. ............. 600/116 |
| 2004/0122450 A1 | 6/2004 | Oren et al. |
| 2004/0172046 A1 | 9/2004 | Hlavka et al. |
| 2004/0181238 A1 | 9/2004 | Zarbatany et al. |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119673 A1 | 6/2005 | Gordon et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0241656 A1 | 10/2006 | Starksen et al. |
| 2006/0264975 A1 | 11/2006 | Pipenhagen et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St.Goar et al. |
| 2007/0049942 A1 | 3/2007 | Hindrichs et al. |
| 2007/0051377 A1 | 3/2007 | Douk et al. |
| 2007/0112424 A1 | 5/2007 | Spence et al. |

FOREIGN PATENT DOCUMENTS

| | | |
|---|---|---|
| WO | WO-94/03227 A1 | 2/1994 |
| WO | WO-96/08208 A1 | 3/1996 |
| WO | WO-98/07375 A1 | 2/1998 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/54618 A1 | 8/2001 |
| WO | WO-02/03892 A1 | 1/2002 |
| WO | WO-02/051329 A1 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |

| | | | |
|---|---|---|---|
| WO | WO-2005/025644 A2 | 3/2005 |
| WO | WO-2005/062931 A2 | 7/2005 |
| WO | WO-2005/062931 A3 | 7/2005 |
| WO | WO-2005/102181 A1 | 11/2005 |
| WO | WO-2006/034243 A2 | 3/2006 |
| WO | WO-2006/034243 A3 | 3/2006 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/100409 A2 | 9/2007 |

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardio.* 71(11):926-931.

De Simone, R. et al. (Apr. 1, 1994). "Adjustable Annuloplasty for Tricuspid Insufficiency with External Control," Reader's Comments and Reply, *Am. J. Cardio.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.

Nagy, Z.L. et al. (2000). "Mitral Annuloplasty with a Suture Technique," *European Journal of Cardio-thoracic Surgery* 18:739-740.

Shumway, S.J. et al. (Dec. 1988). "A 'Designer' Annuplasty Ring for Patients with Massive Mitral Annular Dilatation," *Ann. Thorac. Surg.* 46:695-696.

International Search Report mailed on Apr. 2, 2007, for PCT Application No. PCT/US2006/043597, filed Nov. 8, 2006, seven pages.

* cited by examiner

CARDIAC VISUALIZATION DEVICES AND METHODS

CROSS REFERENCE TO RELATED APPLICATIONS

This application claims the benefit of U.S. Application 60/500,733 filed on Sep. 3, 2003.

BACKGROUND OF THE INVENTION

1. Field of the Invention

The present invention relates generally to medical devices and methods. More particularly, the invention relates to visualization devices and methods for facilitating cardiac surgical procedures, such as repair of the mitral or tricuspid valve for treating mitral or tricuspid regurgitation.

In recent years, many advances have been made to reduce the invasiveness of cardiac surgery. In an attempt to avoid open, stopped-heart procedures, which may be accompanied by high patient morbidity and mortality, many devices and methods have been developed for operating on a heart through smaller incisions, operating on a beating heart, and even performing cardiac procedures via transvascular access. Different types of cardiac procedures, such as cardiac ablation techniques for treating atrial fibrillation, stenting procedures for atherosclerosis, and valve repair procedures for treating conditions such as mitral regurgitation have experienced significant technological advances. In implementing many, if not all, transvascular, minimally invasive and other cardiac surgery techniques, visualization of the heart, the surgical field, surrounding structures, and the like is essential. At the same time, visualization is often difficult, due to the rapid movement of a beating heart as well as the large quantities of pumping blood in an intracardiac surgical field.

One type of cardiac surgery which may benefit from less invasive techniques is heart valve repair. Traditional treatment of heart valve stenosis or regurgitation, such as mitral or tricuspid regurgitation, typically involves an open-heart surgical procedure to replace or repair the valve. Valve repair procedures typically involve annuloplasty, a set of techniques designed to restore the valve annulus shape and strengthen the annulus. Conventional annuloplasty surgery generally requires a large incision into the thorax of the patient (a thoracotomy), and sometimes a median sternotomy (cutting through the middle of the sternum). These open heart, open chest procedures routinely involve placing the patient on a cardiopulmonary bypass machine for sustained periods so that the patient's heart and lungs can be artificially stopped during the procedure. Finally, valve repair and replacement procedures are typically technically challenging and require a relatively large incision through the wall of the heart to access the valve.

Due to the highly invasive nature of open heart valve repair or replacement, many patients, such as elderly patients, patients having recently undergone other surgical procedures, patients with comorbid medical conditions, children, late-stage heart failure patients, and the like, are often considered too high-risk to undergo heart valve surgery and are relegated to progressive deterioration and cardiac enlargement. Often, such patients have no feasible alternative treatments for their heart valve conditions.

To obviate this situation, a number of devices and methods for repairing a mitral valve to treat mitral regurgitation in a less invasive manner have been developed. Some devices provide for heart valve repair through minimally invasive incisions or intravascularly, while others improve upon open heart surgical procedures on beating hearts, stopped hearts or both. For example, several improved devices and methods for heart valve repair are described in one or more patent applications filed by the inventors of the present invention and assigned to the assignee of the present invention. For further description of such devices and methods, reference may be made to U.S. patent application Ser. No. 10/461043, filed on Jun. 13, 2003, which is hereby incorporated fully by reference.

As mentioned above, one of the main challenges in performing minimally invasive surgery on a heart, heart valve, or any other structure is obtaining adequate visualization of the structure and the surgical field. Visualizing a cardiac valve annulus in a beating heart procedure is especially challenging due to rapid movement of the annulus and the heart, the small size of the annulus, and the blood-filled surgical field. Current visualization of minimally invasive cardiac procedures is typically accomplished via transesophageal echocardiogram (TEE). Although this technique works relatively well for some cardiac procedures, it does not provide as clear a picture of the surgical site as would direct visualization. Thus, TEE may not be sufficient for visualizing a minimally invasive procedure within the heart, especially a beating heart procedure to repair a valve annulus.

To obtain direct visualization within the heart, any suitable endoscopic device may be introduced into the heart, such as a conventional endoscope or ultrasonic probe. One problem encountered with such devices, however, is that their ability to provide visualization is often severely reduced by the presence of blood in the heart that surrounds the optic element of the visualization device. A number of devices have been described to combat this problem. For example, U.S. Pat. No. 6,346,074, issued to Roth on Feb. 12, 2002, describes an endoscope having a distal balloon over its end. Such devices still have certain shortcomings, however. For example, balloon-covered endoscope devices are typically introduced into the surgical site through a sheath or introducer device separately from any of the instruments used to perform the cardiac procedure. Thus, the visualization device must typically be manipulated apart from the surgical instruments, and the optical element of the device may often be positioned significantly apart from the working ends of the instruments and the surgical site. In other balloon endoscope devices, the endoscope must be advanced to the surgical site to visualize the site and then removed to allow a surgical instrument to be advanced through the same sheath to perform the procedure. Obviously, such a technique may require numerous, awkward switch-outs of endoscope and surgical instrument and will not result in direct, real-time visualization of the procedure.

Many minimally invasive or "less invasive" surgical procedures other than heart valve repair would also benefit from improved visualization. For example, improved visualization could facilitate other cardiac procedures, such as accessing the coronary sinus for placement of an implantable device or for performing a procedure, placing pacemaker leads in one or more areas of the heart, ablation procedures such as ablation around the pulmonary veins to treat atrial fibrillation, atrial-septal defect repair procedures, and the like. Improved visualization could also be used to enhance non-cardiac procedures such cinching or otherwise treating a bladder, stomach, gastroesophageal junction, vascular structure, gall bladder or the like.

Therefore, it would be beneficial to have improved visualization devices and methods for use in transvascular, minimally invasive and other "less invasive" surgical procedures, such as heart valve repair and other cardiac procedures. Devices and methods for providing such visualization would ideally be minimally invasive and would enhance a physician's ability to locate, visualize and repair a valve annulus, atrial-septal defect, or other cardiac structure accurately and efficiently. Ideally, visualization of the surgical site would be as direct as possible, with an optic element of the visualization device being positioned close to the site. Also ideally, the visualization device would provide visualization at the same time that the physician was performing the procedure and further provide or facilitate access for surgical and/or diagnostic instruments to operate in the visualized field. At least some of these objectives will be met by the present invention.

2. Description of the Background Art

U.S. Pat. No. 6,346,074 describes an endoscope having a balloon over its distal end for use in intracardiac surgery. Patent publications related to mitral valve repair include WO01/26586; US2002/0163784A12; US2002/0156526; US2002/0042621; 2002/0087169; US2001/0005787; US2001/0014800; US2002/0013621; US2002/0029080; US2002/0035361; US2002/0042621; US2002/0095167; and US2003/0074012. U.S. patents related to mitral valve repair include U.S. Pat. Nos. 4,014,492; 4,042,979; 4,043,504; 4,055,861; 4,700,250; 5,366,479; 5,450,860; 5,571,215; 5,674,279; 5,709,695; 5,752,518; 5,848,969;5,860,992; 5,904,651; 5,961,539; 5,972,004; 6,165,183; 6,197,017; 6,250,308; 6,260,552; 6,283,993; 6,269,819; 6,312,447; 6,332,893; and 6,524,338. Publications of interest include De Simone et al. (1993) *Am. J. Cardiol.* 73:721-722 and Downing et al. (2001) *Heart Surgery Forum*, Abstract 7025.

BRIEF SUMMARY OF THE INVENTION

Devices and methods of the present invention facilitate transvascular, minimally invasive and other "less invasive" surgical procedures, such as heart valve repair procedures, by providing direct visualization of a surgical site. "Less invasive," for the purposes of this application, means any procedure that is less invasive than traditional, large-incision open surgical procedures. Thus, a less invasive procedure may be an open surgical procedure involving one or more smaller incisions, a transvascular percutaneous procedure, a transvascular procedure via cut-down, a laparoscopic procedure, or the like. Generally, any procedure in which a goal is to minimize or reduce invasiveness to the patient may be considered less invasive. Furthermore, although the terms "less invasive" and "minimally invasive" may sometimes be used interchangeably in this application, neither these nor other descriptive terms should be interpreted to limit the scope of the invention. Generally, visualization devices and methods of the invention may be used in performing or enhancing any suitable procedure.

In addition to facilitating visualization, devices and methods of the invention also facilitate access for positioning one or more instruments to the surgical site for performing a procedure. The devices generally include a sheath with an expandable balloon at the distal end, an inflation lumen for expanding the balloon, and a device passage lumen for allowing passage of one or more surgical instruments. The sheath is configured to house at least one visualization device such that an optical element of the device is positioned to view the surgical site. In some embodiments, instruments may be passed through the sheath, with the distal balloon partially or fully circumscribing or encircling the instruments. In other embodiments, the balloon may be adjacent, but not encircling, a lumen for instrument passage. Any suitable instrument(s) may be passed through sheaths of the invention, such as a surgical clip applier for repairing a heart valve, an ablation member for treating atrial fibrillation, a suturing device, and/or the like. By positioning a lumen for passage of instruments adjacent a balloon-covered visualization device, sheaths of the present invention provide improved, direct visualization of a surgical site for performing a procedure.

As mentioned above, the present application often focuses on visualization devices and methods as used in heart valve repair, and more specifically mitral valve repair to treat mitral regurgitation. It should be emphasized, however, that visualization devices and methods of the invention may be used in any suitable procedure, both cardiac and non-cardiac. For example, they may be used in procedures to repair the aortic or pulmonary valve, to repair an atrial-septal defect, to access and possibly perform a procedure from the coronary sinus, to place one or more pacemaker leads, to perform a cardiac ablation procedure, and/or the like. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve and other heart valve repair, such description should not be interpreted to limit the scope of the invention as defined by the claims.

That being said, in one aspect of the invention, a method for performing a procedure on a heart involves first advancing an elongate sheath to a location in the heart for performing the procedure. Next, an expandable balloon coupled with a distal end of the elongate sheath is inflated and the location in the heart is visualized through the expandable balloon, using at least one visualization device disposed in the elongate sheath. Finally, at least part of the procedure is performed using one or more instruments extending through a first lumen of the elongate sheath.

In some embodiments, the elongate sheath may be flexible so that it may be advanced through the vasculature of a patient to position at least a distal portion of the sheath in the heart. For example, the sheath may be advanced through the internal jugular vein, superior vena cava, right atrium and interatrial septum of the patient to position the distal portion of the sheath in the left atrium. Alternatively, the sheath may be advanced through the internal jugular vein, superior vena cava, right atrium, coronary sinus and left atrial wall of the patient to position the distal portion of the sheath in the left atrium. In still another embodiment, a flexible sheath may be advanced through the femoral vein, inferior vena cava, right atrium and interatrial septum. In other embodiments, the sheath may be rigid and may be introduced via thorascopically or otherwise through the heart wall.

Inflating the balloon typically involves injecting a fluid into the balloon via a second lumen in the sheath, though any other inflation method may be used. The balloon may have any shape, such as a toroidal balloon encircling the first lumen or a spherical or ovoid balloon adjacent the first lumen. Optionally, methods may further include passing at least one fluid through the first lumen to flush the location for performing the procedure and/or to cleanse one or more instruments positioned in the first lumen. Also optionally, a method may include retracting an outer tubular member to expose additional expandable balloon material from the distal end of the sheath and further inflating the expandable balloon.

The visualizing step may be performed using any suitable visualization device in any location. For example, a fiberoptic viewing scope, typically in combination with a fiberoptic or other illuminator may be used. Another embodiment may employ a charge coupled device with illumination, essentially a small camera, for visualization. In some embodiments, the visualization device is disposed within the elongate sheath for visualizing the surgical site. Sometimes, the visualization device is disposed in a second lumen of the sheath, the second lumen comprising an inflation lumen for inflating the expandable balloon. In some embodiments, a separate visualization device may be passed into the sheath through the second lumen to position the visualization device for visualizing the location. In some embodiments, the visualization device is disposed between an outer tubular member and an inner tubular member of the sheath. The annular space between the two tubular members may also act as an inflation lumen.

Optionally, the method may include visualizing a first view of the location with the visualization device in a first position in the sheath, moving the visualization device to at least a second position in the sheath, and visualizing a second view of the location with the visualization device in the second position. Thus, two or more different views of a surgical site may be acquired using the sheath device and one visualization device. Alternatively, visualization of multiple views may be accomplished via a plurality of visualization devices disposed at various positions in the sheath, for example, disposed at different circumferential positions surrounding a central device passage lumen. In these and other embodiments, a central processing unit may be used to process captured images of the surgical site. Such processed images may then be transmitted proximally for viewing by the physician. For example, in one embodiment visualization may be achieved using a light source and one or more sensors or detectors disposed in a 360-degree array around an inner, device-passage lumen, the light source and the detectors disposed at the distal end of a visualization device. The sensors may then be coupled with a charge coupled device (CCD) disposed near the distal end of the device, the CCD being coupled with a wire that transmits data proximally along the visualization device.

Any suitable surgical procedure may be performed using the devices and methods of the invention. Typically, the procedures will be transvascular, minimally invasive, or other "less invasive" procedures, as discussed above. In some embodiments, the procedure involves repairing a heart valve, such as a mitral, tricuspid, aortic or pulmonary valve. For example, repairing the valve may involve applying clips to a valve annulus using a clip applier extending through the first lumen of the sheath. Such a procedure may further include cinching a tether coupled with the applied clips to decrease a diameter of the valve annulus. In some embodiments, the procedure may be further enhanced by passing a fluid, such as saline, through the first lumen in a direction from a proximal end of the sheath toward the distal end of the sheath to cleanse the surgical instrument(s), clear an area around the surgical site, and/or cleanse the external surface of the balloon.

In another aspect, a device for facilitating a procedure on a heart includes an elongate sheath having a proximal end, a distal end, a first lumen extending from the proximal end to the distal end, and at least a second lumen, and an expandable balloon coupled with the elongate sheath at or near the distal end, wherein the balloon at least partially encircles the first lumen, and the second lumen opens into the balloon for inflating the balloon. The elongate sheath may include one or more rigid tubular members and/or one or more flexible tubular members. In some embodiments, for example, the sheath includes an inner tubular member having an inner surface defining the first lumen and an outer tubular member disposed over the inner tubular member. In such embodiments, the annular space between the inner tubular member and the outer tubular member may form the second lumen.

The expandable balloon may be coupled with the inner tubular member and the outer tubular member at or near the distal end of the sheath such that the second lumen acts as an inflation lumen. Such a balloon may be toroidal in shape, for example, with the first lumen being continuous with a central aperture in the toroidal balloon. Optionally, the outer member may be slidable proximally to expose additional material of the expandable balloon to allow the balloon to further expand. In an alternative embodiment, an slidable outer sleeve may be disposed over the outer tubular member to provide for additional exposure and expansion of an expandable balloon.

The sheath may also include at least one visualization device disposed within the second lumen. For example, the visualization device may include one or more fiber optic devices, ultrasound transducers, charge coupled devices, cameras, light sources and/or sensors. In some embodiments, the distal end of the visualization device is disposed within the expandable balloon. Also in some embodiments, the visualization device is movable within the sheath. For example, where the sheath comprises an inner tubular member and an outer tubular member and the second lumen comprises an annular space between the inner and outer tubular members, the visualization member may be movable around the circumference of the second lumen. In alternative embodiments, the sheath may not include a visualization device but may have a lumen, such as the second lumen, that is sufficiently large to allow passage of at least one visualization device to position a distal end of the device within the expandable balloon.

In some embodiments, the inner diameter of the first lumen is sufficiently large to allow passage of at least one instrument for performing the procedure on the heart. A variety of surgical instruments may thus be passed, though they will often be catheter-based, transvascular, or other less invasive instruments. In one embodiment, the instrument is clip applier for applying a plurality of tethered clips to a valve annulus of the heart and cinching a tether coupled with the clips to reduce a diameter of the valve. In another embodiment, the instrument may be an ablation member for ablating a portion of the heart, such as in a procedure to treat atrial fibrillation.

In another aspect of the invention, a device for facilitating a procedure on a heart includes an elongate sheath having a proximal end, a distal end, a first lumen extending from the proximal end to the distal end, and at least a second lumen, and an expandable balloon coupled with the elongate sheath at or near the distal end and adjacent the first lumen, wherein the second lumen opens into the balloon for inflating the balloon. Unlike the embodiment just described, here the surgical instrument(s) may pass adjacent to but not through the balloon. Typically, in such embodiments, the balloon will have a spherical, ovoid or other suitable shape, but will not be toroidal or "donut-shaped" as in the embodiments described above. These and other embodiments are described more fully below, with reference to the appended drawing figures.

DETAILED DESCRIPTION OF THE INVENTION

Devices and methods for facilitating transvascular, minimally invasive and other "less invasive" surgical procedures generally include a sheath with an expandable balloon at the distal end, an inflation lumen for expanding the balloon, and a device passage lumen for allowing passage of one or more surgical instruments. The sheath is configured to house at least one visualization device such that an optical element of the device is positioned to view the surgical site. In some embodiments, instruments may be passed through the sheath, with the distal balloon partially or fully circumscribing or encircling the instruments. In other embodiments, the balloon may be adjacent, but not encircling, a lumen for instrument passage. Any suitable instrument(s) may be passed through sheaths of the invention, such as a surgical clip applier for repairing a heart valve, an ablation member for treating atrial fibrillation, a suturing device, and/or the like. By positioning a lumen for passage of instruments adjacent a balloon-covered visualization device, sheaths of the present invention provide improved, direct visualization of a surgical site for performing a procedure.

As discussed above, the present application often focuses on visualization devices and methods as used in heart valve repair, and more specifically mitral valve repair to treat mitral regurgitation. It should be emphasized, however, that visualization devices and methods of the invention may be used in any suitable procedure, both cardiac and non-cardiac. For example, they may be used in procedures to repair the aortic or pulmonary valve, to repair an atrial-septal defect, to access and possibly perform a procedure from the coronary sinus, to place one or more pacemaker leads, to perform a cardiac ablation procedure, and/or the like. In other embodiments, the devices and methods may be used to enhance a laparoscopic or other endoscopic procedure on any part of the body, such as the bladder, stomach, gastroesophageal junction, vasculature, gall bladder, or the like. Therefore, although the following description typically focuses on mitral valve and other heart valve repair, such description should not be interpreted to limit the scope of the invention as defined by the claims.

Figure 1:
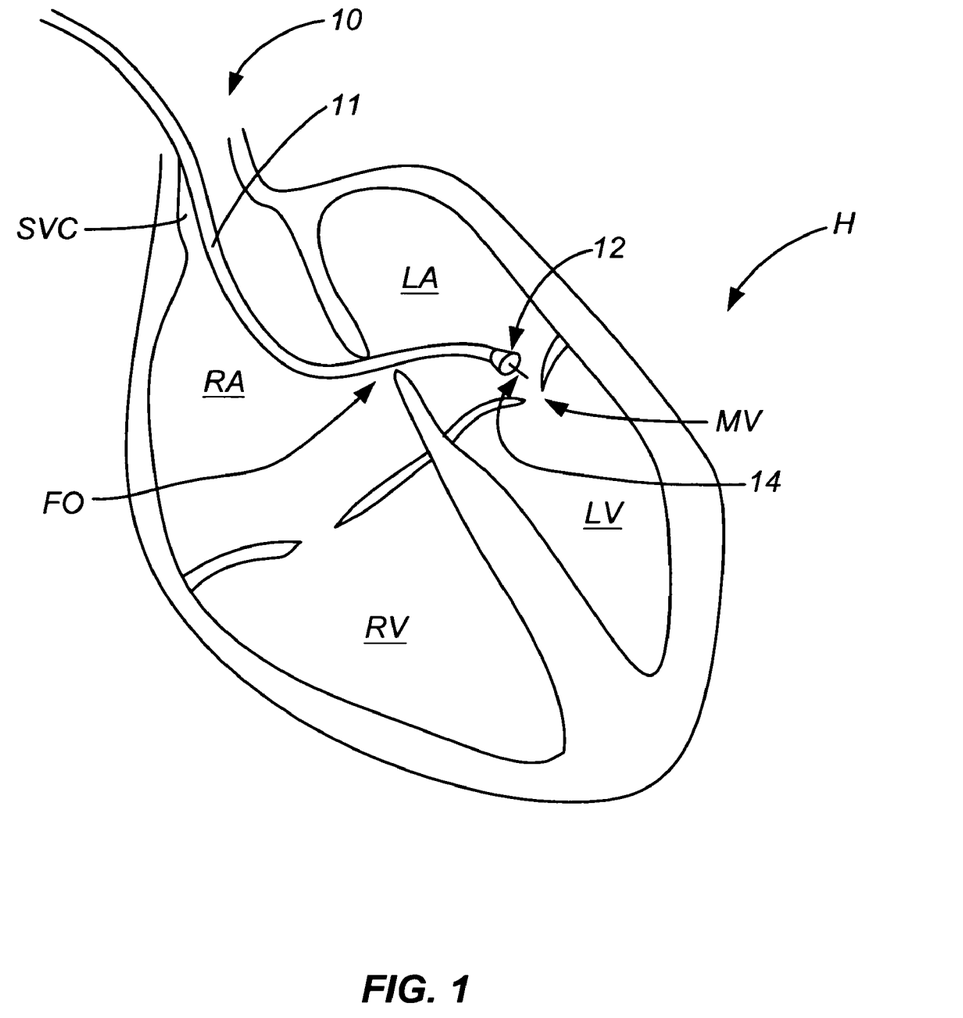
FIG. 1 is a frontal, cross-sectional view of a human heart with a visualization device positioned for performing an intracardiac procedure, in accordance with one embodiment of the present invention.

That being said, and referring now to FIG. 1, an exemplary sheath 10 of the present invention suitably comprises an elongate tubular member 11 having a distal end and a proximal end. An expandable balloon 12 is typically coupled with sheath 10 at or near the distal end, and one or more treatment devices 14 may be passed through an aperture in the distal end. One or more visualization devices (not shown) may be coupled with or inserted into sheath 10 such that an optical element of the visualization device(s) extends up to or within balloon 12.

Generally, sheath 10 may be flexible, rigid, or part-flexible part-rigid, and may be introduced to a surgical site via any suitable method or route. In FIG. 1, for example, sheath 10 has been advanced to the mitral valve MV of a heart H through the superior vena cava SVC, right atrium RA, foramen ovale FO, and left atrium LA. Access to the superior vena cava SVC may be gained, for example, via the internal jugular vein. In other embodiments, access to the RA may be gained through the femoral vein and the inferior vena cava. Thus, access to the heart H may be achieved via a transvascular route. Alternatively, sheath 10 may be introduced through an incision and/or access port in the wall of the left atrium LA. Such access is discussed more fully in U.S. patent application Ser. No. 10/461043, previously incorporated by reference. Any other suitable minimally invasive means for gaining access may alternatively be used to position sheath 10 in a desired location for visualizing and performing a procedure.

Figure 2:
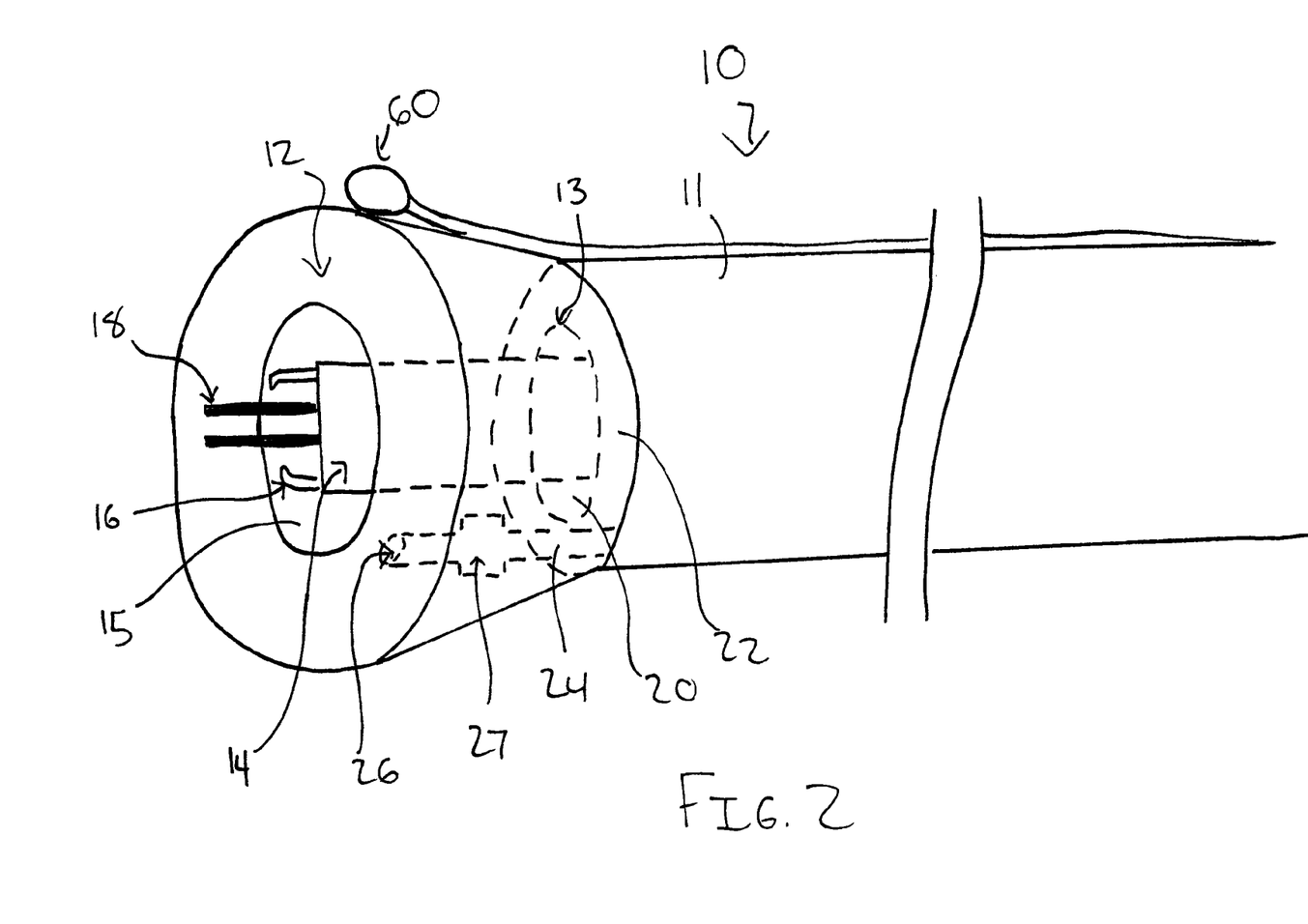
FIG. 2 is a perspective view of a visualization device for performing a minimally invasive cardiac procedure, in accordance with one embodiment of the present invention.
Figure 3:
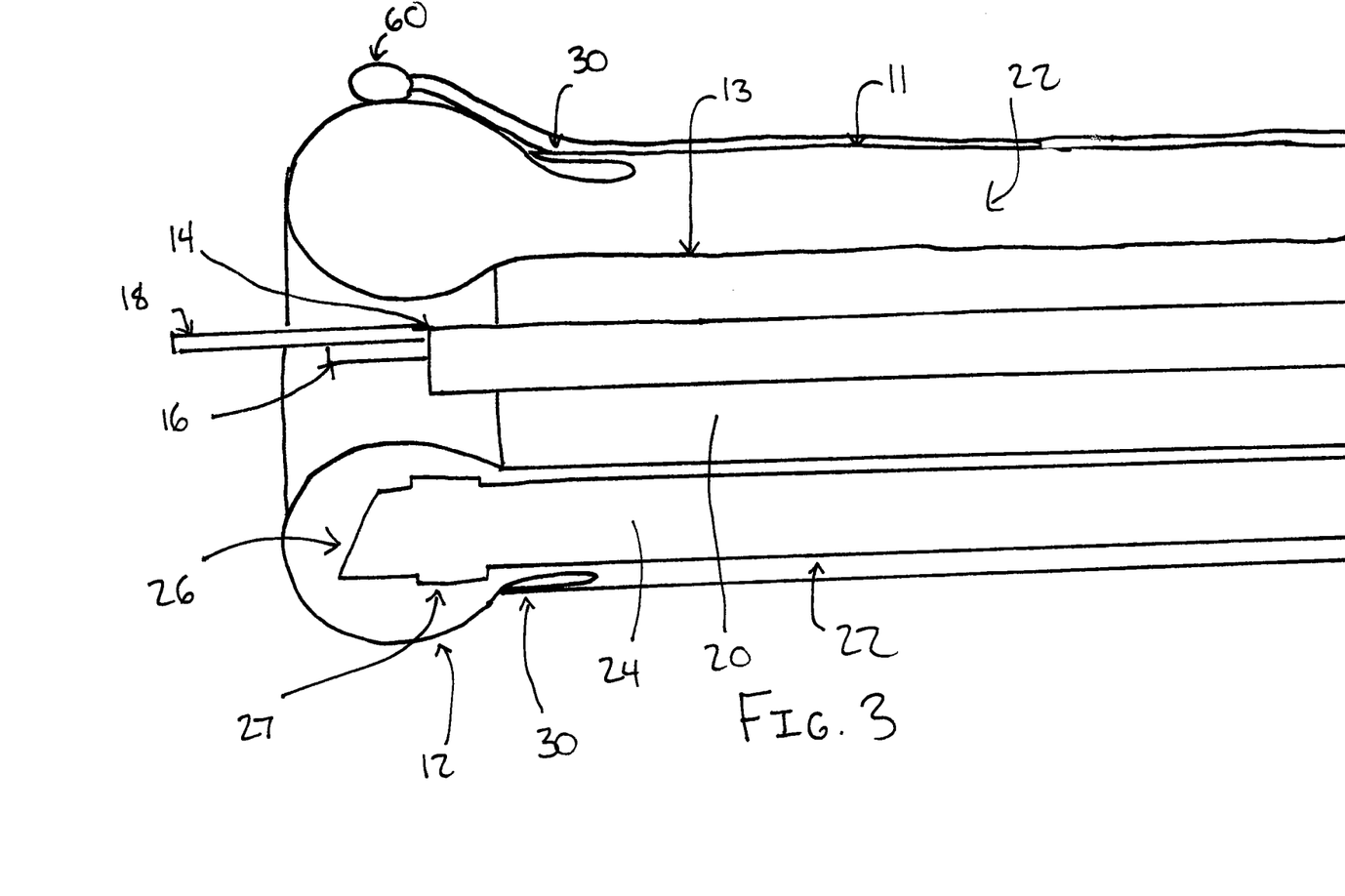
FIG. 3 is a side, cross-sectional view of the visualization device in FIG. 2.

Referring now to FIGS. 2 and 3, one embodiment of sheath 10 suitably includes an outer tubular member 11 and an inner tubular member 13, with the annular space between the two tubular members comprising an inflation lumen 22 and the space within inner tubular member 13 comprising a device passage lumen 20. An expandable balloon 12 is coupled with at least one of the two tubular members at or near the distal end of sheath 10. In FIGS. 2 and 3, balloon 12 is coupled with both tubular members such that inflation lumen 22 opens distally into balloon 12. In this embodiment, balloon 12 has a toroidal or "donut" shape, such that balloon 12 encircles device passage lumen 20, and an aperture 15 in balloon 12 allows one or more treatment devices 14 to extend from the distal end of device passage lumen 20 through balloon 12. A visualization device 24 is disposed within inflation lumen 22 such that a distal portion of visualization device 24, including an optical element 26, extends into balloon 12. Treatment device 14 in this embodiment comprises a clip applier for applying tethered clips to a heart valve annulus, shown with a protruding clip 16 and clip tether 18. Clip appliers for heart valve repair are described more fully in U.S. patent application Ser. No. 10/461043, previously incorporated by reference. Of course, any other suitable treatment device may alternatively be used with sheath 10, such as a hook applier, a suture applier, an ablation device, a scalpel or other cutting device such as an electrocautery device, and/or the like.

Inner tubular member 13 and outer tubular member 11 of sheath 10 may comprise any suitable material or combination of materials and may have any suitable shape, size, diameters, thicknesses and the like. In various embodiments, tubular members 11, 13 may be flexible along their entire lengths, rigid along their entire lengths or part-flexible, part-rigid. The members 11, 13 may be composed of one or more metals, such as Nitinol, stainless steel or titanium; flexible or rigid polymers, such as polyurethane, polytetrafluoroethylene (PTFE), other fluoropolymers, PEBAX®, and/or the like; or any other suitable material or combination of materials. In some embodiments, tubular members 11, 13 may be rigidly fixed to one another, while in other embodiments one of the members 11, 13 may be movable relative to the other. For example, in one embodiment outer tubular member 11 is slidably disposed over inner tubular member 13 so that it can retract proximally over inner tubular member 13 and then extend back distally to its original position.

As shown in FIG. 3, a slidable outer tubular member 11 may allow the size of balloon 12 to be adjusted by a user. Balloon 12 may be coupled with outer tubular member 11 at an attachment point 30 such that sliding outer tubular member 11 proximally and introducing additional fluid or other inflating substance into balloon 12 will cause balloon 12 to further expand. Any suitable configuration of balloon material and attachment point 30 may be used. In one embodiment, for example, balloon material may be housed in a small slit or housing coupled with outer tubular member 11.

In an alternative embodiment, outer tubular member 11 may be fixed, rather than slidable, and an outer, slidable sleeve (not shown) may be disposed over outer tubular member 11. The outer, slidable sleeve may be moved distally to contain part of balloon 12 and moved proximally to release part of balloon 12 to allow for additional expansion. Allowing a user to adjust the size of balloon 12 by sliding outer tubular member 11 proximally or distally and possibly by introducing additional inflation fluid may improve the users ability to visualize the surgical site. Balloon expansion, for example, may help exclude additional blood and/or push aside surrounding tissue from the surgical site.

It may sometimes be advantageous to introduce a fluid substance into device passage lumen 20 to cleanse devices, cleanse balloon 12, clear an area around the surgical site and/or the like. In one embodiment, for example, saline may be introduced proximally with sufficient force to propel it forward (distally) through device passage lumen 20 to "flush" lumen 20. Introduction of saline or other fluids may be accomplished via any suitable proximal inlet, such as a valve on a Y-connector device or the like.

Balloon 12 may have any suitable size, shape and configuration and may be made from any suitable expandable material. Although a toroidal balloon is shown in FIGS. 2 and 3, alternative embodiments may include a spherical, ovoid or otherwise shaped balloon disposed adjacent a lumen for instrument passage but not encircling the lumen. Such an embodiment is described further below with reference to FIG. 4. Similarly, any suitable inflation lumen may be included in sheath 10 for expanding balloon 12. In some embodiments, inflation lumen 22 is formed by the annular space between outer tubular member 11 and inner tubular member 13. Thus, inflation lumen 22 may comprise a circumferential lumen. Alternatively, one or more tubular lumens may be disposed within the annular space between outer tubular member 11 and inner tubular member 13. Any means for inflating balloon 12 is contemplated within the scope of the invention. Typically, balloon 12 is inflated by introducing a fluid, such as saline, into balloon 12 via inflation lumen 22, although any other inflation technique or substance may be used.

Similarly, device passage lumen 20 may have any suitable size, diameter and the like and may be disposed in any location through sheath 10. Thus, device passage lumen 20 may open into aperture 15 through balloon 12, or may alternatively open adjacent (but not through) balloon 12. Lumen 20 may allow passage of any suitable device or devices, such as a surgical clip applier 14 for applying clips 16, coupled with a tether 18, to a heart valve annulus. In other embodiments, ablation devices, electrocautery devices, suturing devices, cutting devices, and/or the like may be passed through device passage lumen 20. Again, any and all suitable devices are contemplated.

Sheath 10 may also include one or more visualization devices 24. In some embodiments, visualization device 24 is included as part of sheath 10, while in other embodiments, a separate visualization device 24 may be inserted into sheath 10 by a user. These latter embodiments may allow, for example, a physician to use an already-owned visualization device or other device with sheath 10. Visualization device 24 itself may comprise any suitable device, such as a fiber optic device, a Doppler crystal or other an ultrasonic device, a charge coupled device, a camera, or the like. In embodiments where visualization device 24 is included, it may be couple with sheath 10 in any suitable manner. For example, visualization device 24 may be disposed within inflation lumen 22 in such a way that it can move within lumen 22. In an embodiment as shown in FIGS. 2 and 3, a visualization device 24 may be movable around the circumference of inflation lumen 22, thus encircling device passage lumen 20. Such movement allows a user to acquire views of the surgical site from multiple angles. In some variations, a Doppler crystal 60 may be disposed on the outer surface of balloon 12.

In some embodiments, multiple visualization devices 24 or a visualization device disposed around a length of the distal end of sheath 10 may be used to visualize the site from multiple angles. To further enhance visualization, some embodiments may include a central processing unit (CPU) 27 at or near the distal end of sheath 10 for processing images captured by visualization device 24. Processed images could then be transmitted proximally along sheath 10 to provide images to the user. For example, in one embodiment visualization may be achieved using a light source and one or more sensors or detectors disposed in a 360-degree array around an inner, device-passage lumen, the light source and the detectors disposed at the distal end of a visualization device. The sensors may then be coupled with a charge couple device (CCD) disposed near the distal end of the device, the CCD being coupled with a wire that transmits data proximally along the visualization device.

Although visualization device 24 is shown with a distal portion and optical element 26 extending into balloon 12, in other embodiments optical element may be flush with, or recessed into, the distal end of inner tubular member 13 and/or outer tubular member 11. Thus, there is no requirement that any visualization member extend into balloon 12. Such a configuration may be advantageous, in that optical element 26 may be positioned closer to clip applier 14 or other devices and closer to the surgical site. If an angled optical element is used, it may be further advantageous to have the optical element facing centrally towards the surgical instrument(s) (or in another direction towards the instrument(s) in other embodiments).

Figure 4:
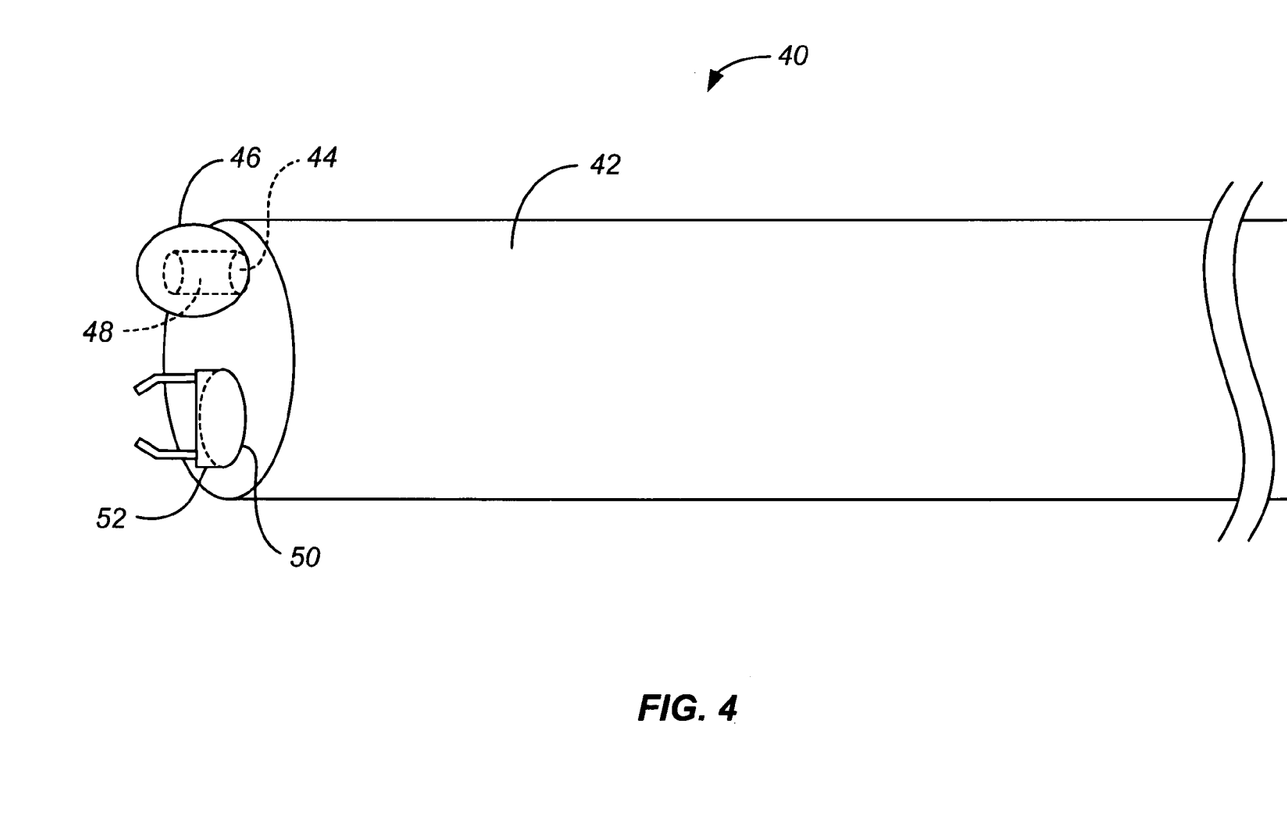
FIG. 4 is a perspective view of a visualization device for performing a minimally invasive cardiac procedure, in accordance with another embodiment of the present invention.

Referring now to FIG. 4, an alternative embodiment of a sheath 40 includes an outer tubular member 42, an inflation lumen 44, a balloon 46, a visualization device 48, and a device passage lumen 50 for allowing passage of one or more surgical instruments 52. In contrast to the earlier described embodiment, inflation lumen 44 does not encircle device passage lumen 50, but instead the two lumens are adjacent one another. The two lumens may be placed at any suitable location through sheath 40 and may exit sheath 40 at any suitable locations, though preferably visualization device 48 will be relative close to device passage lumen 50 to allow for direct visualization of any surgical instruments passed through the lumen 50. In an alternative embodiment, multiple inflation lumens 44, multiple balloons 46 and/or multiple visualization devices 48 may be included. As with the previously described embodiments, some sheaths will include one or more visualization devices 48 while others will simply allow for insertion of a user's visualization device.

Methods of the present invention generally involve first advancing sheath 10, 40 to a location in the heart for performing a minimally invasive heart procedure, such as a mitral or tricuspid valve repair. Next, expandable balloon 12, 46 is inflated and visualization device 24, 48 is used to visualize an area within the heart, locate an area for performing the surgical procedure, etc. The minimally invasive procedure may then be performed, using one or more instruments 14, 52 extending through device passage lumen 20, 50. During the procedure, real-time visualization may be acquired via visualization device 24, 48. Even before the procedure, visualization device 24, 48 may be used to assess the surgical site, locate a particular structure such as a mitral valve annulus, and reposition sheath 10, 40 for better access to the site. In many embodiments, visualization device 24, 48 may be moved within sheath 10, 40 and/or multiple visualization devices may be used to acquire images from different perspectives and angles. Multiple surgical instruments may be inserted and removed through sheath, various visualization devices may be inserted and removed, adjustments to the size of balloon 12, 46 may be made, and/or the like. In some embodiments, the physician may also flush one or more portions of sheath with a fluid passed through one of the sheath's lumens. Any other suitable method steps may be added, steps may be skipped or combined, and or alternative steps may be substituted without departing from the scope of the invention.

Although various embodiments of the present invention have been described fully above, this description is for exemplary purposes only and should not be interpreted to limit the scope of the invention. For example, various alterations, additions, substitutions or the like may be made to embodiments described above without departing from the scope of the invention. Therefore, none of the foregoing description should be read to limit the scope of the invention as it is defined in the following claims.

Any and all patents, applications and printed publications mentioned above are hereby incorporated by reference.

What is claimed is:

1. A device for facilitating a procedure on a heart, the device comprising:
    an elongate sheath having a proximal end, a distal end, a device passage lumen extending therethrough, and at least one inflation lumen, wherein the elongate sheath comprises an inner tubular member having an inner surface defining the device passage lumen, and an outer tubular member disposed over the inner tubular member, wherein the inflation lumen comprises an annular space between the inner tubular member and the outer tubular member;
    an expandable member coupled with the elongate sheath at or near the distal end, wherein the expandable member defines an aperture, is in fluid communication with the inflation lumen, and extends beyond the distal end of the device passage lumen;
    a visualization device disposed within the inflation lumen; and
    an instrument extendable through the device passage lumen and at least partially through the aperture for performing a procedure.

2. The device of claim 1, wherein the elongate sheath comprises at least one rigid tubular member.

3. The device of claim 1, wherein the elongate sheath comprises at least one flexible tubular member.

4. The device of claim 1, wherein the expandable member is coupled with the inner tubular member and the outer tubular member at or near the distal end of the elongate sheath.

5. The device of claim 1, wherein the outer tubular member is proximally retractable.

6. The device of claim 1, further comprising an outer sleeve slidably disposed over the outer tubular member.

7. The device of claim 1, wherein the at least one visualization device comprises at least one of a fiber optic device, an ultrasound transducer, a charge coupled device, a light source and a camera.

8. The device of claim 1, further comprising at least one Doppler crystal disposed on an outer surface of the expandable member.

9. The device of claim 1, wherein a distal end of the visualization device is disposed within the expandable member.

10. The device of claim 1, wherein the at least one visualization device is movable within the sheath.

11. The device of claim 1, wherein the expandable member is a balloon.

12. A device for facilitating a procedure on a heart, the device comprising:
    an elongate sheath having a proximal end, a distal end, a device passage lumen extending therethrough, and at least one inflation lumen, a visualization device disposed within the inflation lumen, wherein the elongate sheath comprises an inner tubular member and an outer tubular member, and wherein the inflation lumen comprises an annular space between the inner and outer tubular members, wherein the at least one visualization device is movable around the circumference of the inflation lumen;
    an expandable member coupled with the elongate sheath at or near the distal end, wherein the expandable member defines an aperture, is in fluid communication with the inflation lumen, and extends beyond the distal end of the device passage lumen; and
    an instrument extendable through the device passage lumen and at least partially through the aperture for performing a procedure.

* * * * *